May 12, 1959 E. S. BOERNER Plant Pat. 1,834
ROSE PLANT
Filed Oct. 24, 1958
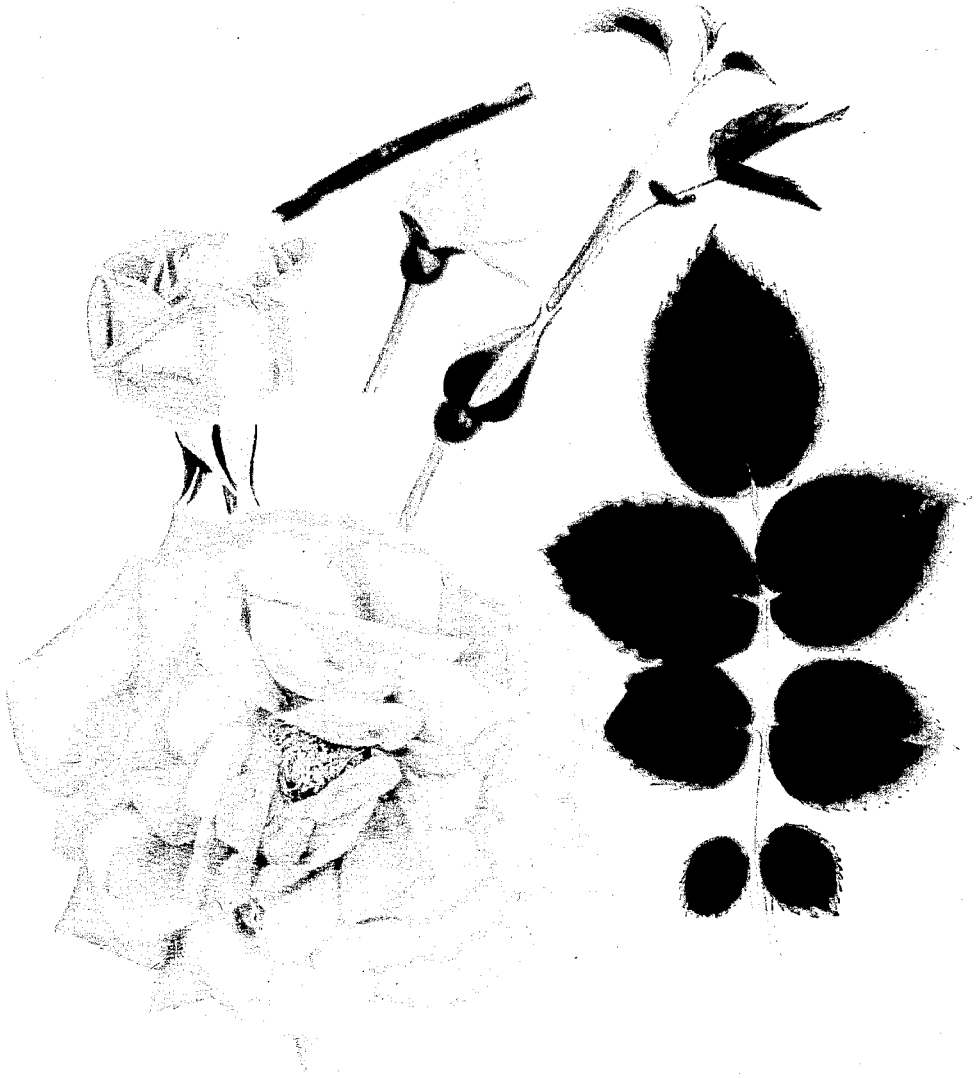
Inventor.
E. S. Boerner
By: Robb & Robb
Attorneys.

United States Patent Office

Plant Pat. 1,834
Patented May 12, 1959

1,834

ROSE PLANT

Eugene S. Boerner, Newark, N.Y., assignor to Jackson & Perkins Company, Newark, N.Y., a corporation of New York Application October 24, 1958, Serial No. 769,526

1 Claim. (Cl. 47—61)

The present invention relates to a new and distinct variety of rose plant of the hybrid tea class, which was originated by me by crossing an unnamed and unpatented red-flowered seedling of "Peace" (Plant Patent No. 591) with an unnamed and unpatented red-flowered hybrid tea seedling.

The primary objective of this breeding was to produce a new rose variety of the red-flowered type which has plant and foliage characteristics corresponding to those of the variety "Peace." To some extent, this objective has been achieved, along with the attainment of other desirable and improved features, and accordingly, the new variety is definitely distinguished from its parents, as well as from all other varieties of which I am aware, as evidenced by the following unique combination of outstanding characteristics:

(1) Large foliage which occurs constantly to the ground;

(2) Large flower size which is unique in flowers of this color;

(3) A characteristic reflexing of the flower petals when the flower opens; and (4) A very bright and distinctive Rose Red, lightly overcast with Tyrian Rose, general color tonality of the flowers.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—An unnamed red seedling of "Peace."
*Pollen parent.*—An unnamed red hybrid tea seedling.
Classification:
*Botanic.*—Hybrid tea.
*Commercial.*—Hybrid tea.

*Flower*

(Observations made from specimens grown in a greenhouse at Newark, New York in the early morning in the early part of March).

Blooming Habit: Recurrent—continuous.
Bud:
*Size.*—Large.
*Form.*—Ovoid: is not affected by wet or hot weather.
*Color.*—When sepals first divide—Carmine, Plate 1. When petals begin to unfurl—Carmine, Plate 1, lightly overcast with Spectrum Red, Plate 1.

When half-blown: inside of petals—Carmine, Plate 1, lightly overcast with Rose Red, Plate 12, with the lower half of the petal lightly overcast with Apricot Yellow, Plate 4; reverse of petals—Rose Red, Plate 12, lightly overcast with Spinel Red, Plate 26, and with lower half of petal lightly overcast with Orange Buff, Plate 3.
*Sepels.*—Slightly branched; curl back when petals begin to unfurl. Color: inside—Light Turtle Green, Plate 32; outside—Cress Green, Plate 31.
*Calyx.*—Color—Cress Green, Plate 31. Shape—apple. Size — large. Aspect — smooth. Odor when rubbed—none.
*Peduncle.* — Length — medium. Aspect — rough. Strength—erect; heavy. Color—Light Bice Green, Plate 17.
*Opening.*—Opens up well; is not affected by adverse weather conditions.
Bloom:
*Size.*—Large. Average size when fully expanded—from 5½ inches to 6 inches.
*Borne.*—Both singly and several together.
*Stems.*—Medium length; strong.
*Form (when first open).*—Cupped. Permanence—Retains its form to the end.
*Petalage.*—Double (full but open center.) Number of petals under normal conditions—from 36 to 40.
*Color.*—Center of flower—Rose Red, Plate 12. Outer petals—Tyrian Rose, Plate 12, lightly overcast with Rose Color, Plate 12. Base of petals (aiglet)—Empire Yellow, Plate 4. Inside of petals—Rose Red, Plate 12, lightly overcast with Tyrian Rose, Plate 12. Reverse of petals—Deep Rose Pink, Plate 12, with lower half of petal lightly overcast with Martius Yellow, Plate 4.
*General tonality from a distance.*—Rose Red, Plate 12.
*Discoloration.*—General tonality at end of first day—Rose Red, Plate 12. Second day—Rose Red, Plate 12. Third day—Rose Red, Plate 12, lightly overcast with Tyrian Rose, Plate 12.
Petals:
*Texture.*—Leathery; is not affected by wet or hot weather.
*Appearance.*—Inside—satiny. Outside—shiny.
*Form.*—Oval; slightly notched.
*Arrangement.*—Imbricated (regularly arranged shingle-like).
*Petaloids in center.*—Few; large.
*Persistence.*—Drop off cleanly.
*Fragrance.*—Moderate. Nature—tea (average hybrid tea scent).
*Lasting quality.*—On the plant—long. As cut flower—long.

*Genital organs*

Stamens, anthers: Large; many; regularly arranged around styles. Color—Mikado Orange, Plate 3.
Stamens, filaments (threads): long. Color—Capucine Buff, Plate 3.
Pollen: Color—Maize Yellow, Plate 4.
Styles: Bunched; uneven length; medium length; thin.
Stigmas: Color—Light Orange-Yellow, Plate 3.
Ovaries: All enclosed in calyx.
Hips: None.
Seeds: None.

*Plant*

Form: Bush.
Growth: Vigorous; upright.
Foliage: Compound of 5–7 leaflets.
*Size.*—Large.

*Quantity.*—Normal.

*Color.*—New foliage: upper side—Lettuce Green, Plate 5, lightly overcast with Oxblood-Red, Plate 1; under side—Oxblood-Red, Plate 1. Old foliage: upper side—Dark Dull Yellow-Green, Plate 32; under side—Light Cress Green, Plate 31.

*Shape.*—Oval pointed.

*Texture.*—Upper side—glossy. Under side—smooth.

*Ribs and veins.*—Ordinary.

*Edge.*—Serrated (saw-toothed).

*Serration.*—Both double and single; deep.

*Leaf stem.*—Color—Lettuce Green, Plate 5. Under side—smooth.

*Stipules.*—Medium length; smooth.

Wood:

*New wood.*—Color—Lettuce Green, Plate 5. Bark—smooth.

*Old wood.*—Color—Cress Green, Plate 31. Bark—smooth.

Thorns:

*Thorns.*—Quantity: on main stalks from base—ordinary; on laterals from stalk—ordinary. Form—narrow base; short; hooked downward. Color (when young)—Begonia Rose, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of large foliage which occurs constantly to the ground, large flower size, a characteristic reflexing of the flower petals when the flower opens, and a very bright and distinctive Rose Red, lightly overcast with Tyrian Rose general color tonality of the flowers.

No references cited.